US012613232B2

(12) United States Patent
Takagi et al.

(10) Patent No.: US 12,613,232 B2
(45) Date of Patent: Apr. 28, 2026

(54) GAS SENSOR SYSTEM

(71) Applicant: Asahi Kasei Microdevices Corporation, Tokyo (JP)

(72) Inventors: Yuta Takagi, Tokyo (JP); Naoya Ugomori, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 492 days.

(21) Appl. No.: 18/187,664

(22) Filed: Mar. 22, 2023

(65) Prior Publication Data

US 2023/0304983 A1 Sep. 28, 2023

(30) Foreign Application Priority Data

Mar. 25, 2022 (JP) ................................. 2022-050733
Mar. 8, 2023 (JP) ................................. 2023-036059

(51) Int. Cl.
| | |
|---|---|
| *G01N 33/98* | (2006.01) |
| *G01N 33/00* | (2006.01) |
| *H05K 7/20* | (2006.01) |
| *G01N 21/3504* | (2014.01) |

(52) U.S. Cl.
CPC ..... *G01N 33/0073* (2013.01); *H05K 7/20209* (2013.01); *G01N 21/3504* (2013.01)

(58) Field of Classification Search
CPC ...................................................... G01N 33/98
See application file for complete search history.

(56) References Cited

U.S. PATENT DOCUMENTS

| | | | | |
|---|---|---|---|---|
| 4,093,945 | A * | 6/1978 | Collier | ................. B60K 28/063 340/576 |
| 2006/0153740 | A1 | 7/2006 | Sultan et al. | |
| 2007/0077176 | A1 | 4/2007 | Lambert et al. | |
| 2009/0272174 | A1* | 11/2009 | Lambert | ............ G01N 33/4972 73/23.3 |
| 2015/0233897 | A1 | 8/2015 | Hok et al. | |

(Continued)

FOREIGN PATENT DOCUMENTS

| | | |
|---|---|---|
| CN | 101975804 A | 2/2011 |
| CN | 104737015 A | 6/2015 |

(Continued)

*Primary Examiner* — John E Breene
*Assistant Examiner* — Alex T Devito
(74) *Attorney, Agent, or Firm* — KENJA IP LAW PC

(57) ABSTRACT

Provided are a gas sensor system, a gas sensor control device, and a control method that enable high-accuracy measurement without causing a user to wait. The gas sensor system (1) includes: a reception section (30) that receives a startup signal from externally to the gas sensor system; a gas sensor (10) that performs concentration measurement of a measurement target gas in air; an air intake port (11) and an air discharge port (12) that are connected to the gas sensor; at least one fan (13); and a control device (20) that starts up the gas sensor through reception of the startup signal, that acquires temperature information for the gas sensor, and that, based on the temperature information for the gas sensor, performs cooling control of operating the fan so as to cool the gas sensor from startup of the gas sensor, before initiation of the concentration measurement.

19 Claims, 7 Drawing Sheets

(56)     References Cited

U.S. PATENT DOCUMENTS

| 2016/0019772 | A1* | 1/2016 | Chacon | G08B 5/36 |
| | | | | 340/573.1 |
| 2019/0324130 | A1 | 10/2019 | Yamamoto et al. | |
| 2019/0346427 | A1 | 11/2019 | Hök et al. | |
| 2020/0166493 | A1 | 5/2020 | Nojiri et al. | |

FOREIGN PATENT DOCUMENTS

| CN | 110389347 | A | 10/2019 |
| CN | 110998305 | A | 4/2020 |
| EP | 3561482 | A1 | 10/2019 |
| JP | 2007147592 | A | 6/2007 |
| JP | 2015114260 | A | 6/2015 |
| JP | 2019023651 | A | 2/2019 |
| JP | 6530652 | B2 | 6/2019 |
| JP | 2020187115 | A | 11/2020 |
| WO | 2010110051 | A1 | 9/2010 |

* cited by examiner

Figure 3:
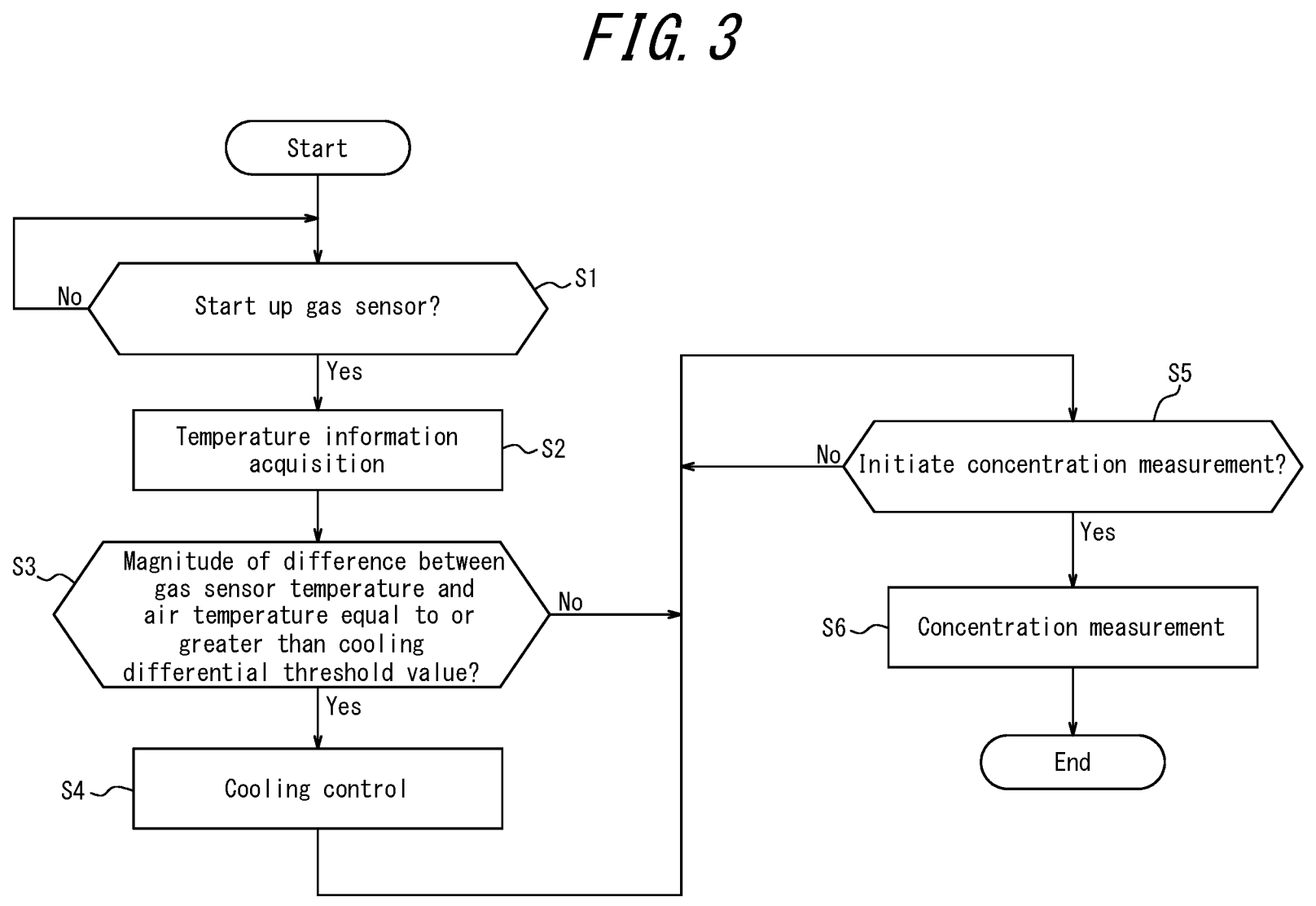

Start

↓

S1 — Start up gas sensor?

No → (loops back to Start)

Yes ↓

S2 — Temperature information acquisition

↓

S3 — Magnitude of difference between gas sensor temperature and air temperature equal to or greater than cooling differential threshold value?

Yes → S4 — Cooling control → (loops back to S3)

No ↓

S5 — Initiate concentration measurement?

No → (loops back)

Yes ↓

S6 — Concentration measurement

↓

End

GAS SENSOR SYSTEM

CROSS-REFERENCE TO RELATED APPLICATIONS

This application claims priority of Japanese Patent Application No. 2022-050733 (filed Mar. 25, 2022) and Japanese Patent Application No. 2023-036059 (filed Mar. 8, 2023), the entire contents of which are incorporated herein by reference.

TECHNICAL FIELD

The present disclosure relates to a gas sensor system, a gas sensor control device, and a control method.

BACKGROUND

Infrared light in a long wavelength band typically having a wavelength of 2 μm or more is used in gas sensors and the like due to a thermal effect thereof and an effect of infrared light absorption by gases. For example, non-dispersive infrared (NDIR) gas sensors are used to measure the concentration of a gas through detection of the amount of absorption of infrared light by exploiting the fact that the wavelength of infrared light that is absorbed differs depending on the type of gas (for example, refer to Patent Literature (PTL) 1).

An example of such a gas sensor is an alcohol sensor that is installed in a vehicle. For example, a breath inspection system described in PTL 2 includes a fan for taking in exhaled air through air flow and stops the fan during detection of the exhaled air in order to accurately judge the alcohol concentration in the exhaled air. Another example of use of gas sensors is as $CO_2$ sensors. A $CO_2$ sensor may be used for air quality monitoring of a vehicle or detecting when someone is left behind, for example.

CITATION LIST

Patent Literature

PTL 1: JP 6530652 B2
PTL 2: JP 2019-023651 A

SUMMARY

Particularly in a situation in which a gas sensor is used outdoors, etc., measurement accuracy of the gas sensor may decrease in a situation in which the temperature of the gas sensor differs significantly from the temperature of the environment of use. Conventional gas sensors deal with such a situation by acquiring the temperature of the gas sensor once a measurement initiation command is received from a user and not initiating measurement until the gas sensor has reached an appropriate temperature or by performing measurement but not making use of a measurement value until an appropriate temperature is reached, for example. This has resulted in time being required until reliable information is obtained through measurement.

In view of the situation set forth above, an object of the present disclosure is to provide a gas sensor system, a gas sensor control device, and a control method that enable high-accuracy measurement without causing a user to wait.

(1) A gas sensor system according to an embodiment of the present disclosure comprises:
   a gas sensor that performs concentration measurement of a measurement target gas in air;

a reception section that receives a startup signal from externally to the gas sensor system;
   an air intake port and an air discharge port that are connected to the gas sensor;
   at least one fan for performing air intake and air discharge from the air intake port and the air discharge port; and
   a control device that starts up the gas sensor through reception of the startup signal, that acquires temperature information for the gas sensor, and that, based on the temperature information for the gas sensor, performs cooling control of operating the fan so as to cool the gas sensor from startup of the gas sensor, before initiation of the concentration measurement.

(2) As an embodiment of the present disclosure, in the foregoing (1),
   the control device performs the cooling control in a situation in which a temperature of the gas sensor is equal to or higher than a cooling threshold value.

(3) As an embodiment of the present disclosure, in the foregoing (1),
   the control device acquires temperature information for a space from which the air intake port takes in air and performs the cooling control based on the temperature information for the gas sensor and the temperature information for the space from which the air intake port takes in air.

(4) As an embodiment of the present disclosure, in the foregoing (3),
   the control device performs the cooling control in a situation in which a magnitude of difference between a temperature of the gas sensor and a temperature of the space from which the air intake port takes in air is equal to or greater than a cooling differential threshold value.

(5) As an embodiment of the present disclosure, in the foregoing (4),
   the cooling differential threshold value is 5° C. or higher.

(6) As an embodiment of the present disclosure, in any one of the foregoing (1) to (5),
   the control device sets operation time of the fan as not more than a fixed time in the cooling control.

(7) As an embodiment of the present disclosure, in any one of the foregoing (1) to (6),
   the control device stops the cooling control based on temperature information for the gas sensor in the cooling control.

(8) As an embodiment of the present disclosure, in any one of the foregoing (1) to (7),
   the control device stops operation of the fan based on a signal from externally to the gas sensor system in the cooling control.

(9) As an embodiment of the present disclosure, in any one of the foregoing (1) to (8),
   the gas sensor system is a system installed in a vehicle, and
   the reception section receives the startup signal from a control device of the vehicle in response to an operation of the vehicle and starts up the gas sensor.

(10) As an embodiment of the present disclosure, in the foregoing (9),
   the operation of the vehicle includes door unlocking of the vehicle.

(11) As an embodiment of the present disclosure, in any one of the foregoing (1) to (10),
   the gas sensor system further comprises a transmission section that transmits a signal indicating that preparation for the concentration measurement is complete.

(12) As an embodiment of the present disclosure, in the foregoing (11), the gas sensor system further comprises a notification section that notifies a user that preparation for the concentration measurement is complete based on the signal of the transmission section.

(13) A gas sensor control device according to an embodiment of the present disclosure acquires temperature information for a gas sensor that performs concentration measurement of a measurement target gas in air and, based on the temperature information for the gas sensor, performs cooling control of operating at least one fan for performing air intake and air discharge from an air intake port and an air discharge port connected to the gas sensor so as to cool the gas sensor from reception of a startup signal, before initiation of the concentration measurement.

(14) A control method according to an embodiment of the present disclosure is a control method performed by a gas sensor system including: a gas sensor that performs concentration measurement of a measurement target gas in air; a reception section that receives a startup signal from externally to the gas sensor system; an air intake port and an air discharge port connected to the gas sensor; at least one fan for performing air intake and air discharge from the air intake port and the air discharge port; and a control device, the control method comprising the control device:

acquiring temperature information for the gas sensor; and based on the temperature information for the gas sensor, operating the fan so as to cool the gas sensor from reception of the startup signal, before initiation of the concentration measurement.

(15) As an embodiment of the present disclosure, in the foregoing (14), the control device operates the fan so as to cool the gas sensor from reception of the startup signal, before initiation of the concentration measurement, based on the temperature information for the gas sensor in a situation in which a temperature of the gas sensor is equal to or higher than a cooling threshold value.

(16) As an embodiment of the present disclosure, in the foregoing (14), the control device acquires temperature information for a space from which the air intake port takes in air and, based on the temperature information for the gas sensor and the temperature information for the space from which the air intake port takes in air, operates the fan so as to cool the gas sensor from reception of the startup signal, before initiation of the concentration measurement.

According to the present disclosure, it is possible to provide a gas sensor system, a gas sensor control device, and a control method that enable high-accuracy measurement without causing a user to wait.

BRIEF DESCRIPTION OF THE DRAWINGS

In the accompanying drawings:

FIG. 3 is a flowchart illustrating an example of a control method according to the first embodiment of the present disclosure;

DETAILED DESCRIPTION

Figure 1:
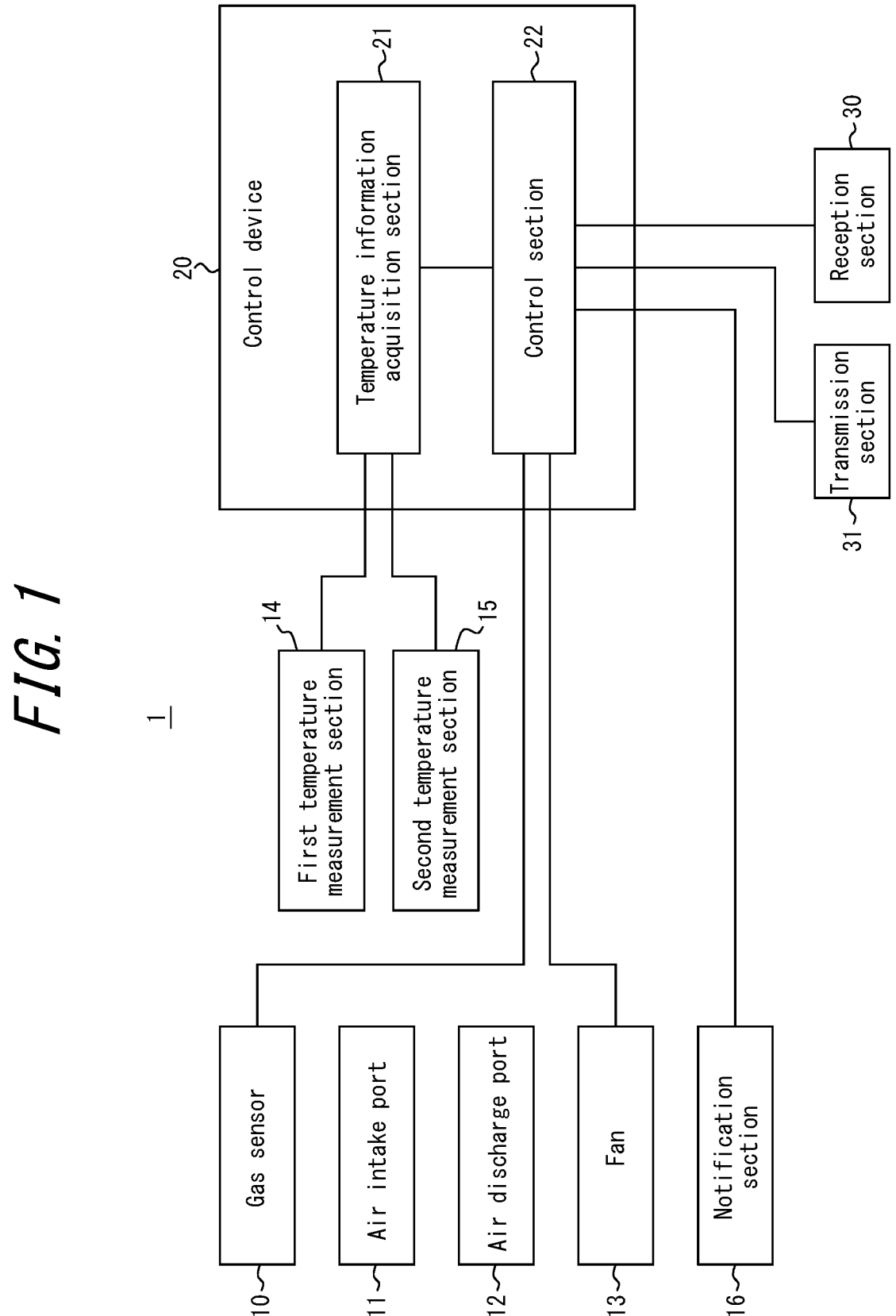
FIG. 1 is a block diagram of a configuration example of a gas sensor system according to a first embodiment of the present disclosure.

The following describes a gas sensor system, a gas sensor control device, and a control method according to an embodiment of the present disclosure with reference to the drawings. Parts in the drawings that are the same or correspond are allotted the same reference signs. In description of the present embodiment, descriptions of parts that are the same or correspond may be omitted or abbreviated as appropriate.

First Embodiment

<Gas Sensor System>

FIG. 1 is a block diagram of a gas sensor system 1 according to a first embodiment. The gas sensor system 1 includes a gas sensor 10, an air intake port 11, an air discharge port 12, a fan 13, a control device 20, a reception section 30, and a transmission section 31. The control device 20 is a gas sensor control device that includes a temperature information acquisition section 21 and a control section 22. The gas sensor system 1 may further include a first temperature measurement section 14, a second temperature measurement section 15, and a notification section 16 as in the present embodiment.

Figure 2:
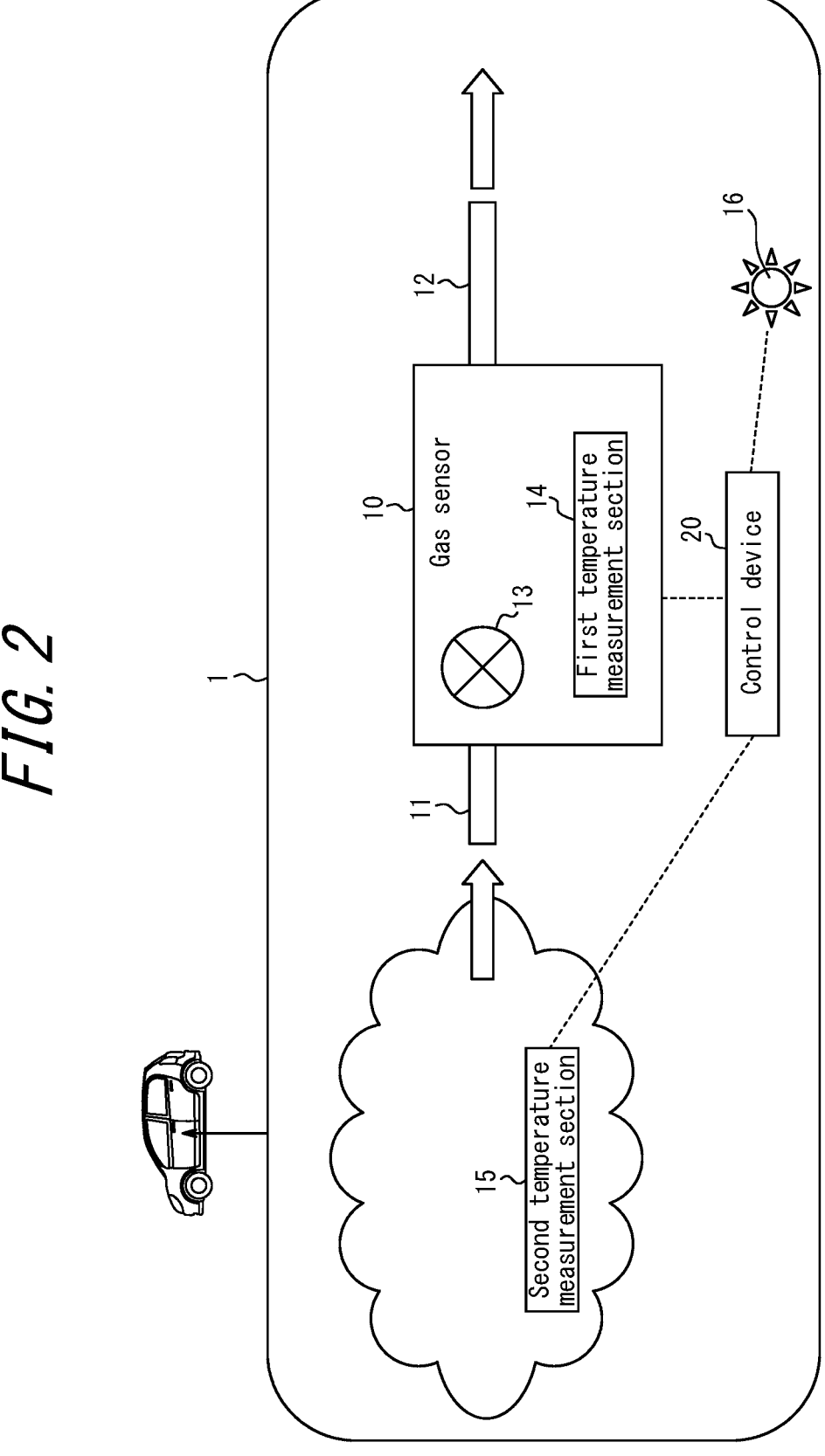
FIG. 2 is a diagram illustrating an application example of the gas sensor system according to the first embodiment of the present disclosure.

FIG. 2 is a diagram illustrating an application example of the gas sensor system 1 according to the present embodiment. The gas sensor system 1 may, for example, be a system that is installed in a vehicle and that performs concentration measurement of a measurement target gas in air inside the vehicle and then performs notification to a person onboard the vehicle and control of the vehicle in accordance with the measurement result. Although no limitations are placed on the use of the gas sensor system 1, the gas sensor system 1 in the present embodiment is used to judge the alcohol concentration in air exhaled by a driver and then place the vehicle in a state in which driving is permitted or in a state in which driving is not permitted in accordance with the judgment result. Users of the gas sensor system 1 in the present embodiment include a driver of the vehicle. In another example, the gas sensor system 1 may be used to measure carbon dioxide concentration in air inside a vehicle and then advise a user to perform ventilation or the like or perform control to automatically perform ventilation in accordance with the measurement result. In this case, users of the gas sensor system 1 include people onboard the vehicle. Moreover, the gas sensor system 1 is not limited to being installed in a vehicle and may, for example, perform concentration measurement of a measurement target gas indoors or inside of an installation.

In a case in which the gas sensor system 1 is installed in a vehicle, the gas sensor system 1 may be set up on a dashboard or the like that can reach a high temperature. When the gas sensor 10 reaches a high temperature, the signal-to-noise ratio (SNR) deteriorates, and measurement accuracy decreases. Accordingly, when measurement is performed with the gas sensor 10 still at a high temperature, the temperature of the gas sensor may become unstable during intake of air because the temperature of the gas sensor itself and the temperature of a space from which air is taken in differ, and thus an erroneous alcohol concentration judgment may be made, and driving of the vehicle may be hindered. This has conventionally been dealt with by, for example, acquiring the temperature of the gas sensor 10 once a measurement initiation command is received from a user, initiating cooling of the gas sensor 10, and not initiating measurement of alcohol concentration or not using a concentration measurement value until the gas sensor 10 reaches an appropriate temperature or the temperature thereof stabilizes. However, there is demand for a system that can initiate alcohol concentration measurement without causing a user to wait since it is desirable for a user that a vehicle starts moving as soon as possible. The gas sensor system 1 according to the present embodiment enables high-accuracy measurement without causing a user to wait through the configuration set forth below. In the present embodiment, a description is given under the presumption that the temperature of the gas sensor 10 is equal to or higher than the temperature of air in the environment of use.

(Gas Sensor)

The gas sensor 10 is a device that performs concentration measurement of a measurement target gas in air. The gas sensor 10 is not specifically limited but may be of an NDIR or photoacoustic type, which are optical types, or may be a gas sensor based on electrochemistry. In an NDIR method, the gas concentration is measured through detection of the amount of absorption of infrared light by exploiting the fact that the wavelength of infrared light that is absorbed differs depending on the type of gas. In a photoacoustic method, the gas concentration is measured through vibrations of gas molecules that have absorbed infrared light being picked up as sound using a high-performance microphone. In an electrochemical method, the gas concentration is measured using a redox reaction. In the following description, the gas sensor 10 in the present embodiment is taken to be an NDIR device.

The gas sensor 10 may include, for example, a light-emitting element that emits infrared light, an optical member that guides infrared light emitted from the light-emitting element to a light-receiving element, a light-receiving element that receives infrared light, a cell (chamber) into which air containing a measurement target gas is introduced, and a computation section that computes a gas concentration. The light-emitting element may be a light bulb, a MEMS light source, or an infrared LED, for example. The light-receiving element may be a quantum infrared sensor such as a photodiode having a PIN structure or a thermopile, for example. The optical member may be a mirror and a lens, for example. The optical member configures an optical path of infrared light from the light-emitting element to the light-receiving element such that it passes through the cell into which air is introduced. The computation section may, for example, compute the received amount of infrared light for which there has been absorption by the measurement target gas from an output signal of the light-receiving element and then compute the gas concentration through comparison of this received amount of light with the received amount of light in a situation in which the measurement target gas is not present. In the present embodiment, the computation section may have functions of alcohol concentration judgment and outputting a judgment result to a control device of the vehicle.

The wavelength of the infrared light may be 2 μm to 12 μm. The region of 2 μm to 12 μm is a wavelength band that is particularly suitable for use in the gas sensor 10 due to a large number of absorption bands that are characteristic of various gases being present in this region. For example, an absorption band for methane is present at a wavelength of 3.3 μm, an absorption band for carbon dioxide is present at a wavelength of 4.3 μm, and an absorption band for alcohol (ethanol) is present at a wavelength of 9.5 μm. In the present embodiment, the measurement target gas includes alcohol, and infrared light of a wavelength band inclusive of 9.5 μm is used.

(Air Intake Port and Air Discharge Port)

The air intake port 11 and the air discharge port 12 are connected to the gas sensor 10. When alcohol concentration measurement is to be performed in the present embodiment, air including exhaled air of a driver is introduced into the cell of the gas sensor 10 from the air intake port 11. Moreover, after alcohol concentration measurement or the like has been performed, air inside the cell of the gas sensor 10 is discharged from the air discharge port 12.

(Reception Section)

A reception section 30 that receives a startup signal is provided in order to start up the gas sensor from an external device. The startup signal is generated based on pre-concentration measurement information. For example, in the present embodiment, the startup signal may be generated from an ECU of the vehicle based on a preliminary operation that precedes boarding of the vehicle. The preliminary operation that precedes boarding of the vehicle may be any operation through which intention to board the vehicle is detected, for example, such as door unlocking, detection of proximity of a remote key to the vehicle, or remote start of the vehicle. The preliminary operation that precedes boarding of the vehicle may be any preliminary operation that precedes an engine or power supply of the vehicle being set to ON, and may include release of a parking brake, pressing of a brake pedal, contact of a shift lever, or detection of sitting in the vehicle. In the case of a gas sensor system that is incorporated into a ventilation fan indoors, the preliminary operation may be detection of intention to use a room. This detection of intention to use a room may be detection of entry into the room where the ventilation fan is installed, switching on lighting of the room, or the like, for example.

(Fan)

At least one fan 13 is provided for performing air intake and air discharge from the air intake port 11 and the air discharge port 12. The fan 13 may be provided externally or internally of the gas sensor 10. A plurality of fans 13 may be provided. The fan 13 may have a structure including a propeller and a motor and may cause air flow through rotation of the propeller. The motor has the propeller attached thereto and may, for example, have an on or off state of rotation and a rotation direction thereof controlled by the control device 20. As described above, the fan 13 operates so as to perform air intake from the air intake port 11 and air discharge from the air discharge port 12 before and after concentration measurement of the measurement target gas. In the present embodiment, the fan 13 can also perform air discharge from the air intake port 11 by setting the rotation direction of the propeller as the reverse of the normal direction.

(Temperature Measurement Section)

The first temperature measurement section 14 measures the temperature of the gas sensor 10 and outputs temperature information that is a signal indicating the measured temperature. Moreover, the second temperature measurement section 15 measures the temperature of a space from which the air intake port takes in air and outputs temperature information that is a signal indicating the measured temperature. In the following description, the first temperature measurement section 14 and the second temperature measurement section 15 may be referred to collectively as the "temperature measurement section" when no distinction is made therebetween. Also, the "temperature of a space from which the air intake port takes in air" is also denoted as "air temperature" in the drawings, etc. The temperature measurement section may be a temperature sensor such as a thermistor, for example. The gas sensor system 1 may have a configuration in which at least one of the first temperature measurement section 14 and the second temperature measurement section 15 is not included in order to reduce the number of constituent components and enable miniaturization. In such a configuration, the temperature information acquisition section 21 may, for example, acquire temperature information for the gas sensor 10 from the computation section included in the gas sensor 10. Moreover, the temperature information acquisition section 21 may, for example, acquire temperature information for the space from which the air intake port takes in air from the control device of the vehicle. In a case in which the temperature information acquisition section 21 does not include a thermometer, the temperature information acquisition section 21 can, in place thereof, receive temperature information from an external device that is not included in the gas sensor system.

(Transmission Section)

The transmission section 31 transmits a signal for notifying that preparation for concentration measurement of the measurement target gas is complete. Preparation for concentration measurement of the measurement target gas may be judged to be complete based on the temperature of the gas sensor or may be judged to be complete based on non-uniformity or temporal variation of the temperature of the gas sensor. Moreover, a judgment may be made based not only on the temperature of the gas sensor, but also based on temperature information for air in the space from which air is taken in.

(Notification Section)

The notification section 16 is a device that notifies the user that preparation for concentration measurement of the measurement target gas is complete based on the signal of the transmission section 31. The notification section 16 may acquire a signal indicating that preparation is complete from the transmission section 31. Although no limitations are placed on the configuration of the notification section 16, the notification section 16 may include a light that notifies completion of preparation through light as in the present embodiment or may include a speaker that notifies completion of preparation through sound. The notification section 16 may, for example, perform display on a display or the like that is present on a dashboard. Through the notification section 16, it is possible for the user to clearly realize that concentration measurement of the measurement target gas can be performed. The gas sensor system 1 may have a configuration in which the notification section 16 is not included in order to reduce the number of constituent components and enable miniaturization.

<Control Device>

In the present embodiment, the control device 20 includes the temperature information acquisition section 21 and the control section 22. The control device 20 may be a device including hardware specialized for control or a processor that performs computation and control. For example, the control device 20 may be implemented by a microcontroller unit.

Functions of the temperature information acquisition section 21 and the control section 22 may be implemented by software or may be implemented by hardware. For example, at least one program may be stored in a storage device that can be accessed by a processor included in the control device 20. The program stored in the storage device may cause the control device 20 to function as the temperature information acquisition section 21 and the control section 22 when the program is read by the processor included in the control device 20.

(Temperature Information Acquisition Section)

The temperature information acquisition section 21 acquires temperature information for the gas sensor 10. In the present embodiment, the temperature information acquisition section 21 also acquires temperature information for the space from which the air intake port takes in air. The temperature information acquisition section 21 acquires the temperature information from startup of the gas sensor 10, before initiation of concentration measurement of the measurement target gas. The temperature information acquisition section 21 outputs the acquired temperature information to the control section 22.

(Control Section)

The control section 22 controls operation of the gas sensor 10 and the fan 13. The control section 22 performs cooling control of operating the fan 13 so as to cool the gas sensor 10 based on the temperature information for the gas sensor 10. Air flow generated through operation of the fan 13 can cool the gas sensor 10 and can lower the temperature of the gas sensor 10 that is at a high temperature. The temperature of the gas sensor 10 can also be lowered by taking in air that is of a lower temperature than the gas sensor 10. In the present embodiment, the control section 22 performs the cooling control based on the temperature information for the gas sensor 10 and the temperature information for the space from which the air intake port takes in air. More specifically, the control section 22 performs the cooling control in a situation in which the magnitude of difference between the temperature of the gas sensor 10 and the temperature of the space from which the air intake port takes in air is equal to or greater than a cooling differential threshold value. The cooling differential threshold value may be set in accordance with the average temperature of an environment in which the vehicle is used, for example. As one example, the cooling differential threshold value may be 5° C., but is not specifically limited thereto. The cooling differential threshold value may be set to 5° C. or higher, for example. Also, the cooling differential threshold value may be set to 50° C. or less, for example. A smaller differential threshold value means that more time is taken for preparation, but that the accuracy of measurement increases because the temperature of the gas sensor stabilizes. Moreover, a larger differential threshold value means that preparation is completed at an earlier stage, but that the accuracy of measurement tends to decrease.

The control section 22 performs the cooling control from reception of the startup signal, before initiation of concentration measurement of the measurement target gas. In other words, at a time at which the user attempts to perform concentration measurement of the measurement target gas (inclusive of starting up an application that uses a concentration measurement result of the gas sensor 10), the gas sensor 10 that is at a high temperature has been cooled and preparation for measurement is complete, or at least the waiting time until measurement can be performed has been shortened. Herein, "measurement can be performed" is inclusive of it being possible to treat a measurement value as a reliable value. Consequently, high-accuracy measurement can be performed without causing the user to wait. In order for the control section 22 to perform the cooling control before initiation of concentration measurement of the measurement target gas, it is necessary for the control section 22 to detect a state in which the gas sensor 10 can be used (startup timing of the gas sensor 10). In the present embodiment, the control section 22 acquires a signal indicating door unlocking from the vehicle and starts up the gas sensor 10 in a situation in which door unlocking has been performed. The control section 22 may acquire a signal of door unlocking from the control device of the vehicle. Information pertaining to boarding of the vehicle other than door unlocking may alternatively be used as a trigger. For example, the gas sensor 10 may start up in response to an operation such as door unlocking, detection of proximity of a remote key to the vehicle, or remote start of the vehicle. When the control section 22 starts up the gas sensor 10, the control section 22 judges whether the magnitude of temperature difference is equal to or greater than the cooling differential threshold value based on temperature information for the gas sensor 10 and temperature information for the space from which the air intake port takes in air. In a situation in which the magnitude of temperature difference is equal to or greater than the cooling differential threshold value, the control section 22 performs the cooling control and lowers the temperature of the gas sensor 10. The control section 22 may perform control so as to lower the temperature of the gas sensor 10 in a situation in which the temperature of the gas sensor 10 is equal to or higher than the temperature of the space from which the air intake port takes in air, for example. Alternatively, the control section 22 may perform control so as to lower the temperature of the gas sensor 10 in a situation in which the temperature of the gas sensor 10 is at least 5° C. higher than the temperature of the space from which the air intake port takes in air, for example. Alternatively, the control section 22 may perform control so as to lower the temperature of the gas sensor 10 in a situation in which the temperature of the gas sensor 10 is at least 10° C. higher than the temperature of the space from which the air intake port takes in air, for example.

Moreover, the control section 22 may acquire a signal indicating that an engine of the vehicle has started and may judge that there has been an initiation command for concentration measurement of the measurement target gas (alcohol concentration measurement in the present embodiment) from the user. The control section 22 may acquire the signal of engine starting from the control device of the vehicle. In a situation in which there has been an initiation command for concentration measurement of the measurement target gas, so long as the gas sensor 10 has been sufficiently cooled and measurement preparation is complete, the control section 22 causes the transmission section 31 to transmit a signal indicating that preparation is complete to the notification section 16 and causes the notification section 16 to notify the user that preparation is complete. Moreover, in a situation in which there has been an initiation command for concentration measurement of the measurement target gas, the control section 22 may cause the notification section 16 to notify that preparation is not complete when further cooling of the gas sensor 10 is required (i.e., when measurement preparation is not complete). No specific limitations are placed on the type of vehicle. Examples thereof include electric vehicles. In the case of an electric vehicle, engine starting described above can also be considered to be a state in which a drive system is operable (drivable state).

The control section 22 may cause the gas sensor 10 to perform concentration measurement of the measurement target gas after completion of measurement preparation. Note that the control section 22 may perform control such as to stop the fan 13 during concentration measurement of the measurement target gas in order to suppress the occurrence of noise and further increase measurement accuracy.

<Control Method>

FIG. 3 is a flowchart illustrating an example of an operation control method performed by the control device 20 of the gas sensor system 1 according to the present embodiment. The control device 20 waits (No in Step S1) until it acquires a signal to start up the gas sensor 10. In the present embodiment, the signal to start up the gas sensor 10 is a signal from the control device of the vehicle that indicates door unlocking.

The control device 20 starts up the gas sensor 10 in a situation in which it has acquired a door unlocking signal (Yes in Step S1) and acquires temperature information (Step S2). In the present embodiment, the temperature information includes temperature information for the gas sensor 10 and temperature information for the space from which the air intake port takes in air.

In a situation in which the magnitude of difference between the temperature of the gas sensor 10 and the temperature of the space from which the air intake port takes in air (i.e., a value obtained by subtracting the temperature of the space from which the air intake port takes in air from the temperature of the gas sensor 10) is equal to or greater than the cooling differential threshold value (Yes in Step S3), the control device 20 performs cooling control (Step S4). This cooling control is control of operating the fan 13 so as to cool the gas sensor as previously described. The temperature of the gas sensor 10 is lowered through this cooling control.

In a situation in which preparation is complete after the cooling control or a situation in which the magnitude of difference between the temperature of the gas sensor 10 and the temperature of the space from which the air intake port takes in air is less than the cooling differential threshold value (No in Step S3), the control device 20 waits (No in Step S5) until it acquires a signal to initiate alcohol concentration measurement. In the present embodiment, the signal to initiate alcohol concentration measurement is a signal from the control device of the vehicle that indicates that the engine of the vehicle has started. This signal to initiate alcohol concentration measurement may be generated with a signal to start the engine as a start point. Moreover, the control device 20 may stop the cooling control based on temperature information for the gas sensor 10 or stop operation of the fan 13 based on an external signal. For example, the control device 20 may stop the cooling control in a situation in which it judges that the temperature of the gas sensor 10 has decreased based on the temperature information. Moreover, the control device 20 may, for example, stop operation or reduce the rotation speed of the fan 13 based on a signal that a driver has sat in the vehicle (one example of an external signal).

In a situation in which the control device 20 has acquired a signal to initiate alcohol concentration measurement (Yes in Step S5), the control device 20 causes the gas sensor 10 to perform concentration measurement of the measurement target gas (Step S6). In a situation in which the control device 20 has acquired a signal to initiate alcohol concentration measurement before preparation is complete after the cooling control, the control device 20 may continue the cooling control and cause the concentration measurement of the measurement target gas to be performed once preparation is complete. Note that concentration measurement of the measurement target gas may, in and of itself, be performed during the cooling control. A concentration measurement result value may be treated as invalid until preparation is complete.

The gas sensor system 1 may not include at least one of the first temperature measurement section 14 and the second temperature measurement section 15 in order to reduce the number of constituent components and enable miniaturization as previously described. For example, in a case in which the gas sensor system 1 does not include the second temperature measurement section 15, the control device 20 may perform the cooling control based only on the temperature information for the gas sensor 10. In this case, the judgment in Step S3 may be for the control device 20 to perform the cooling control in a situation in which the temperature of the gas sensor 10 is equal to or higher than a cooling threshold value. The cooling threshold value may be 40° C., for example. In other words, the control device 20 may perform the cooling control when the temperature of the gas sensor 10 is 40° C. or higher without comparison with the temperature of the space from which the air intake port takes in air. Although 40° C. is given as one example, any condition under which condensation does not occur in a person's exhaled air may be adopted.

In the present embodiment, the control device 20 performs the cooling control through electrical power from a battery of the vehicle. The control device 20 may set the operation time of the fan 13 as not more than a fixed time (60 seconds as one example) in the cooling control in order to not significantly consume electrical power of the battery. In this case, the control device 20 may perform control such as to return to processing in Step S2 when preparation is not complete after performing the cooling control once (i.e., when further cooling of the gas sensor 10 is required). Moreover, the number of times that concentration measurement of the measurement target gas is performed is not limited to once. The concentration measurement of the measurement target gas may include provisional measurement as a test run, for example, and processing in the flowchart in FIG. 3 may be performed repeatedly until measurement for obtaining a final judgment result is performed. Note that the flowchart in FIG. 3 is one example. In a case in which continuous measurement is performed, for example, control returning to processing in Step S2 after Step S6 may be performed.

The cooling control may be performed together with verification of operation of the fan during an initialization process of the gas sensor system. In a case in which it is possible to operate the fan and perform cooling in accompaniment to error detection during an error detection phase in initialization of the gas sensor system, the cooling control and initialization can be performed in parallel, thereby streamlining the system.

In this manner, through the configuration and processing set forth above, the gas sensor system 1, the control device 20, and the control method according to the present embodiment perform cooling control before initiation of measurement in a situation such as when the temperature of the gas sensor 10 is at a high temperature that is equal to or higher than the temperature of a space from which the air intake port takes in air in the environment of use. Therefore, the gas sensor system 1, the control device 20, and the control method according to the present embodiment enable high-accuracy measurement without causing a user to wait.

Second Embodiment

Figure 4:
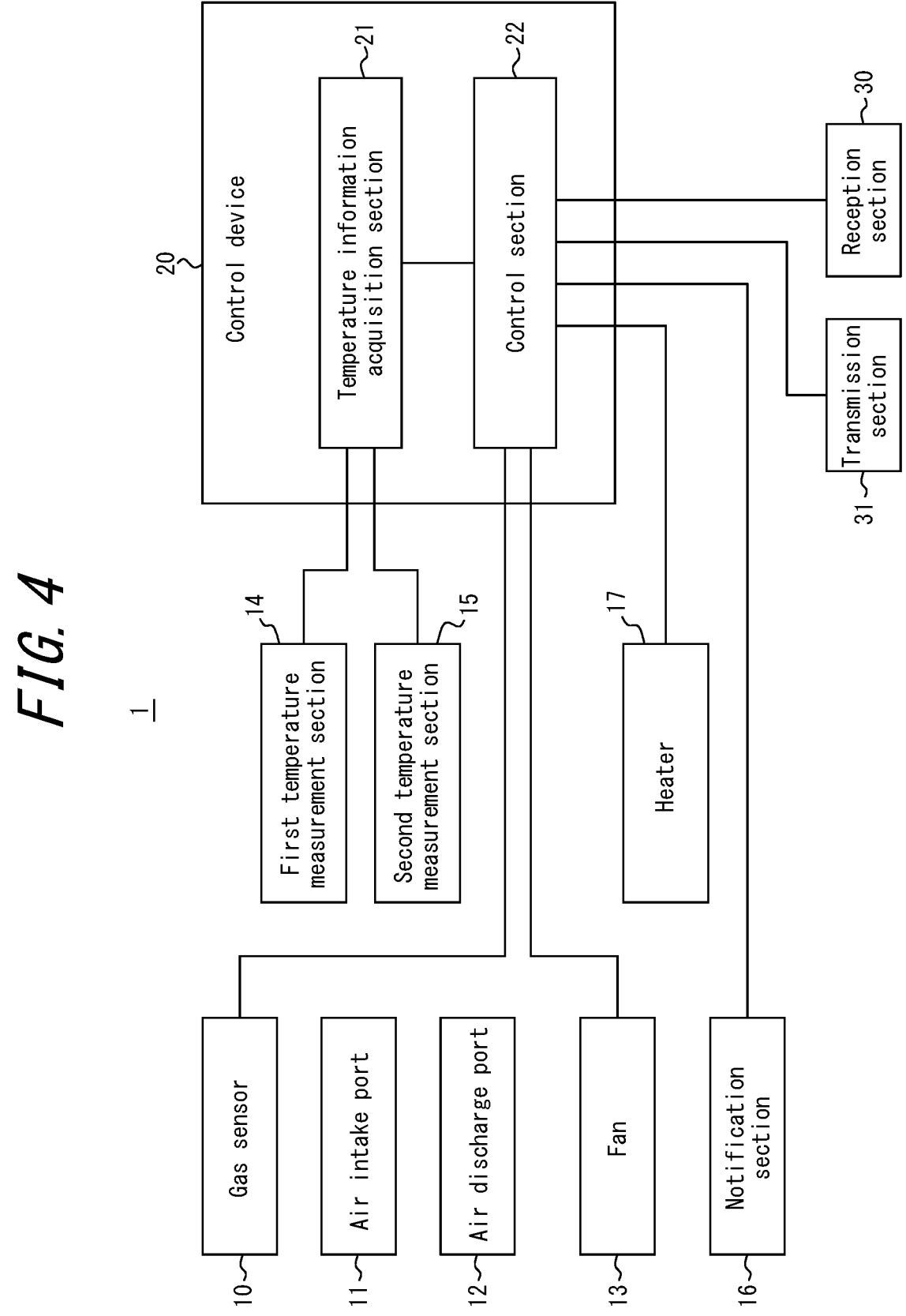
FIG. 4 is a block diagram of a configuration example of a gas sensor system according to a second embodiment of the present disclosure.
Figure 5:
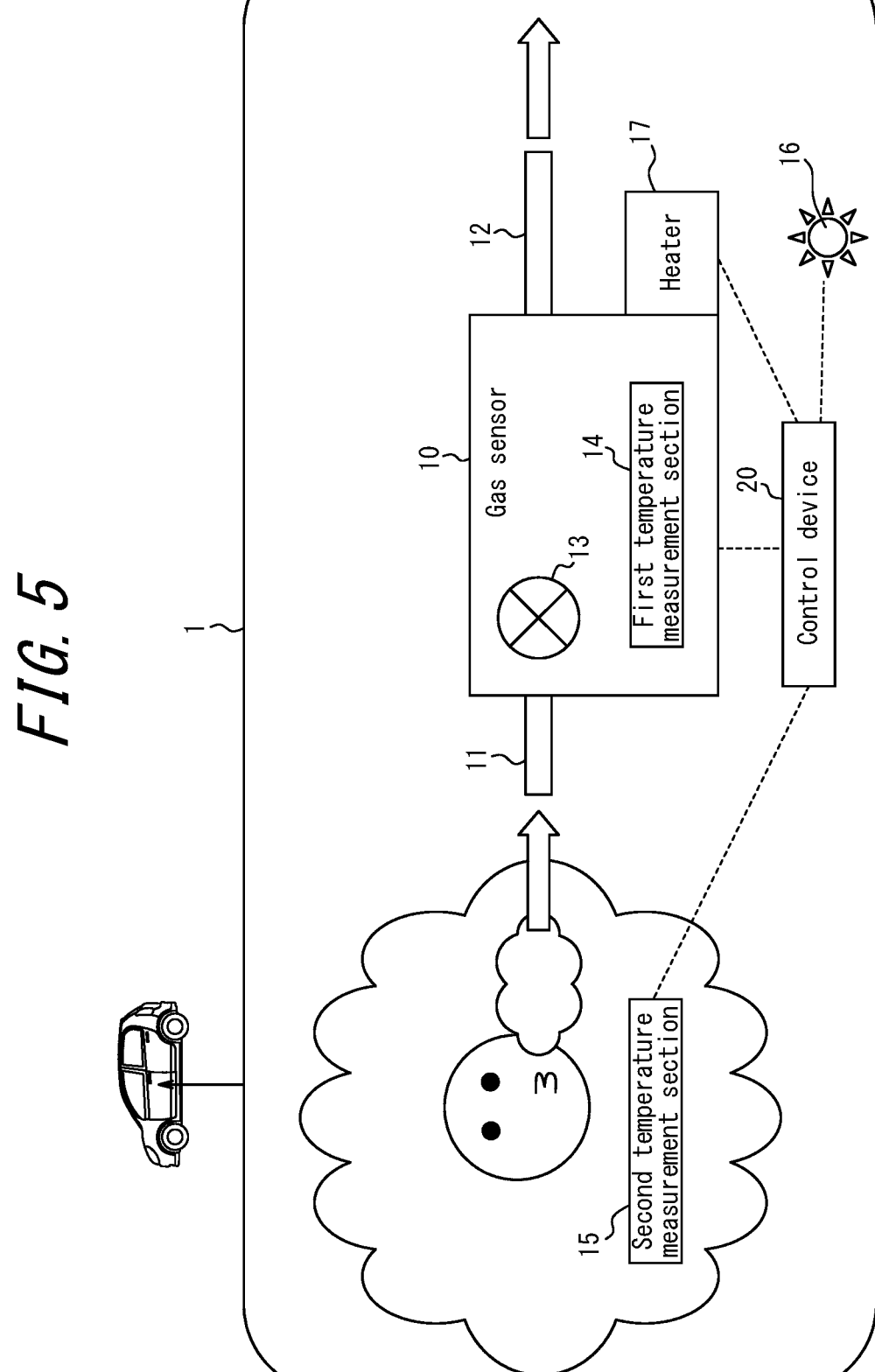
FIG. 5 is a diagram illustrating an application example of the gas sensor system according to the second embodiment of the present disclosure.

FIG. 4 is a block diagram of a gas sensor system 1 according to a second embodiment. The gas sensor system 1 according to the present embodiment further includes a heater 17 in addition to the constituent elements of the gas sensor system 1 according to the first embodiment. FIG. 5 is a diagram illustrating an application example of the gas sensor system 1 according to the present embodiment. Although no limitations are placed on the use of the gas sensor system 1 according to the present embodiment, the gas sensor system 1 is described as a system installed in a vehicle that judges the alcohol concentration in air exhaled by a driver. In order to avoid repeated description, the following describes configurations differing from the first embodiment.

In a case in which the gas sensor system 1 is installed in a vehicle, the gas sensor system 1 may be used in a low temperature environment such as during the winter. In a situation in which air including exhaled air is introduced into the cell while the gas sensor 10 has a low temperature, condensation may form. Particularly when condensation forms on an optical member, absorption and scattering may occur when infrared light is reflected, for example, thereby reducing the amount of light that is received by the light-receiving element. Therefore, condensation reduces measurement accuracy. When measurement is performed with the gas sensor 10 still at a low temperature, an erroneous alcohol concentration judgment may be made, and driving of the vehicle may be hindered. This has conventionally been dealt with by, for example, acquiring the temperature of the gas sensor 10 once a measurement initiation command is received from a user, starting heating of the gas sensor 10, and not initiating measurement of alcohol concentration until the gas sensor 10 reaches an appropriate temperature. However, there is demand for a system that can initiate alcohol concentration measurement without causing a user to wait since it is desirable for a user that a vehicle starts moving as soon as possible. The gas sensor system 1 according to the present embodiment enables high-accuracy measurement without causing a user to wait through the configuration set forth below. In the present embodiment, a description is given under the presumption that the temperature of the gas sensor 10 is lower than the temperature of air in the environment of use.

(Heater)

The heater 17 is a device that heats the gas sensor 10. The heater 17 is arranged in proximity to or inside of the gas sensor 10. The heater 17 may be arranged such that it can at least heat an optical member of the gas sensor 10. Although no limitations are placed on the type of heater 17, the heater 17 may be an electrothermal device that generates heat through passing of current. The heater 17 is controlled to on or off by the control device 20.

(Control Section)

The control section 22 controls operation of the gas sensor 10, the fan 13, and the heater 17. The control section 22 performs heating control of operating the heater 17 so as to heat the gas sensor 10 and air intake blocking control of controlling the fan 13 so as to not take in air from the air intake port 11 based on temperature information for the gas sensor 10. The air intake blocking control is not limited to control of the fan 13 and may be control such that the air intake port or the air discharge port is physically blocked, for example, so long as it is control that can block air intake to a certain extent. In other words, the air intake blocking means by which air intake from the air intake port is blocked may be the fan 13, but is not limited thereto, and may alternatively be a means of physically blocking the air intake port or the air discharge port, for example. The control section 22 warms the gas sensor 10 by operating the heater 17 and prevents relatively warm air from being taken in from the air intake port 11 by controlling the fan 13, and can thereby prevent condensation. In the present embodiment, the control section 22 performs the heating control and the air intake blocking control based on temperature information for the gas sensor 10 and temperature information for a space from which the air intake port takes in air. More specifically, the control section 22 performs at least one of the heating control and the air intake blocking control in a situation in which the magnitude of difference between the temperature of the gas sensor 10 and the temperature of the space from which the air intake port takes in air is equal to or greater than a heating differential threshold value. The heating differential threshold value may be set in accordance with the average temperature of an environment in which the vehicle is used, for example. As one example, the heating differential threshold value may be 5° C., but is not specifically limited thereto. The heating differential threshold value may be set to 5° C. or higher, for example. Also, the heating differential threshold value may be set to 50° C. or less, for example. The heating differential threshold value can also be set as zero. In this case, the heating control is performed when the temperature of the gas sensor 10 is equal to or lower than the temperature of the space from which the air intake port takes in air.

The control section 22 may operate the heater 17 until the temperature of the gas sensor 10 reaches a heating threshold value in the heating control. The heating threshold value may be set as a temperature close to body temperature, for example, and, as one example, may be 36° C.

Control of the fan 13 in the air intake blocking control may, more specifically, be stopping the fan 13 or operating the fan 13 so as to perform air discharge from the air intake port 11. Air discharge can be performed from the air intake port 11 by causing reverse rotation of the propeller of the fan 13 relative to normal rotation. By performing air discharge from the air intake port 11, the effect of condensation prevention can be further enhanced.

The control section 22 performs the heating control and the air intake blocking control from reception of a startup signal, before initiation of concentration measurement of the measurement target gas. In other words, at a time at which the user attempts to perform concentration measurement of the measurement target gas, the gas sensor 10 that is at a low temperature has been heated without condensation and preparation for measurement is complete, or at least the waiting time until measurement can be performed has been shortened. Consequently, high-accuracy measurement can be performed without causing the user to wait. In order to perform the heating control and the air intake blocking control before initiation of concentration measurement of the measurement target gas, the control section 22 acquires a signal indicating door unlocking from the vehicle and starts up the gas sensor 10 in a situation in which door unlocking has been performed, for example, in the same manner as in the first embodiment. The control section 22 may acquire a signal of door unlocking from the control device of the vehicle. When the control section 22 starts up the gas sensor 10, the control section 22 judges whether the temperature is equal to or higher than the heating threshold value based on the temperature information for the gas sensor 10. Alternatively, the control section 22 judges whether the magnitude of temperature difference is equal to or greater than the heating differential threshold value based on the temperature information for the gas sensor 10 and the temperature information for the space from which the air intake port takes in air. In a situation in which the magnitude of temperature difference is equal to or greater than the heating differential threshold value, the control section 22 performs the heating control, raises the temperature of the gas sensor 10, controls the fan 13 so as to not take in air from the air intake port 11, and performs the air intake blocking control.

<Control Method>

Figure 6:
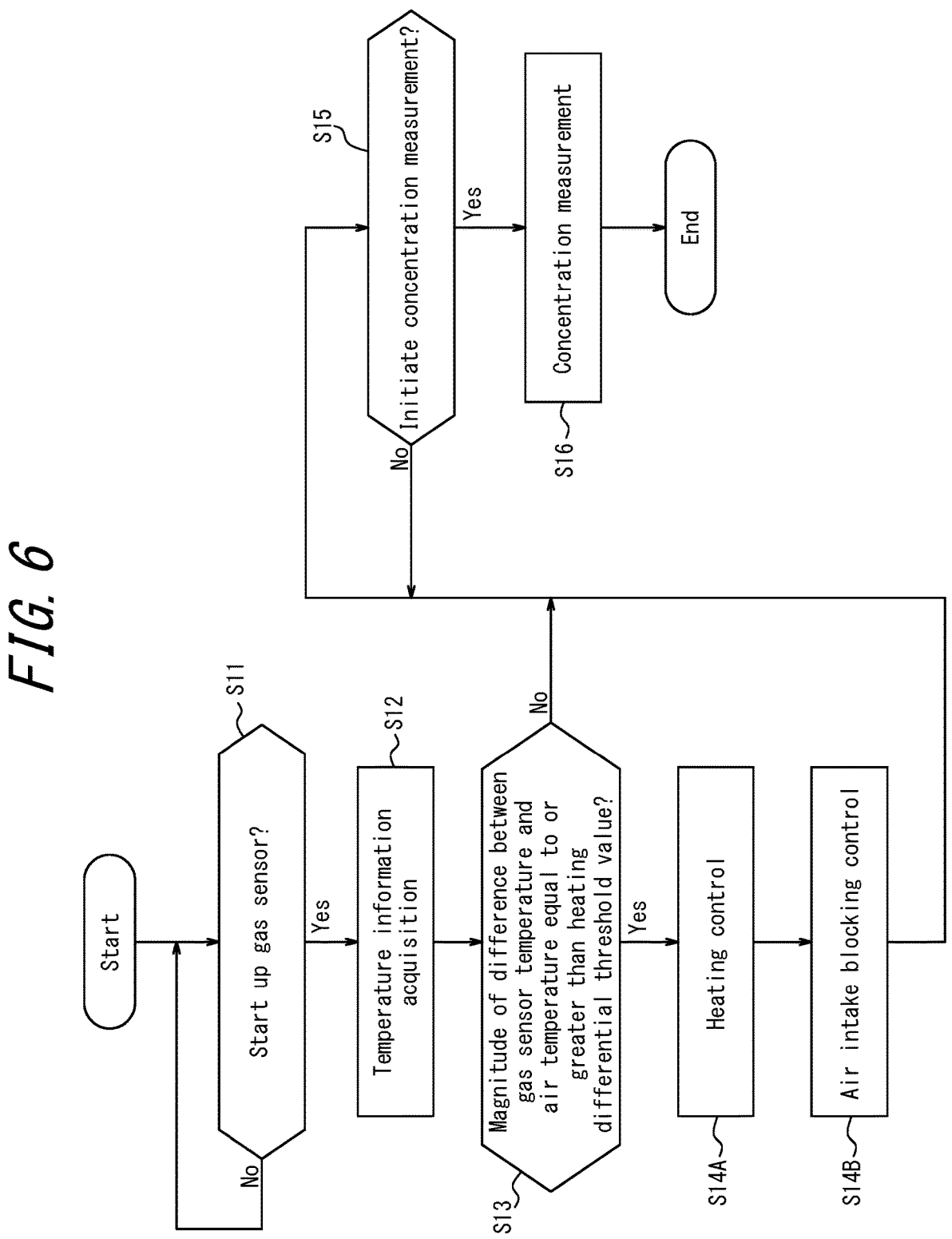
FIG. 6 is a flowchart illustrating an example of a control method according to the second embodiment of the present disclosure.

FIG. 6 is a flowchart illustrating an example of an operation control method performed by the control device 20 of the gas sensor system 1 according to the present embodiment. The control device 20 waits (No in Step S11) until it acquires a signal to start up the gas sensor 10. In the present embodiment, the signal to start up the gas sensor 10 is a signal from the control device of the vehicle that indicates door unlocking.

The control device 20 starts up the gas sensor 10 in a situation in which it has acquired a door unlocking signal (Yes in Step S11) and acquires temperature information (Step S12). In the present embodiment, the temperature information includes temperature information for the gas sensor 10 and temperature information for the space from which the air intake port takes in air.

In a situation in which the magnitude of difference between the temperature of the gas sensor 10 and the temperature of the space from which the air intake port takes in air (i.e., a value obtained by subtracting the temperature of the gas sensor 10 from the temperature of the space from which the air intake port takes in air) is equal to or greater than the heating differential threshold value (Yes in Step S13), the control device 20 performs heating control (Step S14A) and air intake blocking control (Step S14B). This heating control is control of operating the heater 17 so as to heat the gas sensor 10 and controlling the fan 13 so as to not take in air as previously described. The temperature of the gas sensor 10 rises through this heating control, and condensation is prevented through blocking of air intake.

In a situation in which preparation is complete after the heating control or a situation in which the magnitude of difference between the temperature of the gas sensor 10 and the temperature of the space from which the air intake port takes in air is less than the heating differential threshold value (No in Step S13), the control device 20 waits (No in Step S15) until it acquires a signal to initiate alcohol concentration measurement. In the present embodiment, the signal to initiate alcohol concentration measurement is a signal from the control device of the vehicle that indicates that the engine of the vehicle has started.

In a situation in which the control device 20 has acquired a signal to initiate alcohol concentration measurement (Yes in Step S15), the control device 20 causes the gas sensor 10 to perform concentration measurement of the measurement target gas (Step S16). In a situation in which the control device 20 has acquired a signal to initiate alcohol concentration measurement before preparation is complete after the heating control, the control device 20 may continue the heating control and cause the concentration measurement of the measurement target gas to be performed once preparation is complete. Alternatively, idle operation of measurement may be performed during preparation.

The gas sensor system 1 may not include at least one of the first temperature measurement section 14 and the second temperature measurement section 15 in order to reduce the number of constituent components and enable miniaturization as previously described. For example, in a case in which the gas sensor system 1 does not include the second temperature measurement section 15, the control device 20 may perform the heating control and the air intake blocking control based only on the temperature information for the gas sensor 10. In this case, the judgment in Step S13 may be for the control device 20 to perform the heating control and the air intake blocking control in a situation in which the temperature of the gas sensor 10 is lower than a heating threshold value. The heating threshold value may be 36° C., for example. In other words, the control device 20 may perform the heating control and the air intake blocking control when the temperature of the gas sensor 10 is lower than 36° C. without comparison with the temperature of the space from which the air intake port takes in air.

In the present embodiment, the control device 20 performs the heating control and the air intake blocking control through electrical power from a battery of the vehicle. The control device 20 may set the operation time of the fan 13 as not more than a fixed time (60 seconds as one example) in order to not significantly consume electrical power of the battery. In this case, the control device 20 may perform control such as to return to processing in Step S12 when preparation is not complete after performing the heating control once (i.e., when further heating of the gas sensor 10 is required). Moreover, the number of times that concentration measurement of the measurement target gas is performed is not limited to once. The concentration measurement of the measurement target gas may include provisional measurement as a test run, for example, and processing in the flowchart in FIG. 6 may be performed repeatedly until measurement for obtaining a final judgment result is performed.

In this manner, through the configuration and processing set forth above, the gas sensor system 1, the control device 20, and the control method according to the present embodiment perform heating control before initiation of measurement and prevent condensation in a situation such as when the temperature of the gas sensor 10 is at a low temperature that is lower than the temperature of a space from which the air intake port takes in air in the environment of use. Therefore, the gas sensor system 1, the control device 20, and the control method according to the present embodiment enable high-accuracy measurement without causing a user to wait.

Third Embodiment

A block diagram of a gas sensor system 1 according to a third embodiment is the same as for the second embodiment. The gas sensor system 1 according to the present embodiment performs the cooling control or the heating control described above based on temperature information for the gas sensor 10. Although no limitations are placed on the use of the gas sensor system 1 according to the present embodiment, the gas sensor system 1 is described as a system installed in a vehicle that judges the alcohol concentration in air exhaled by a driver. In order to avoid repeated description, the following describes processing differing from the first embodiment and the second embodiment.

Figure 7:
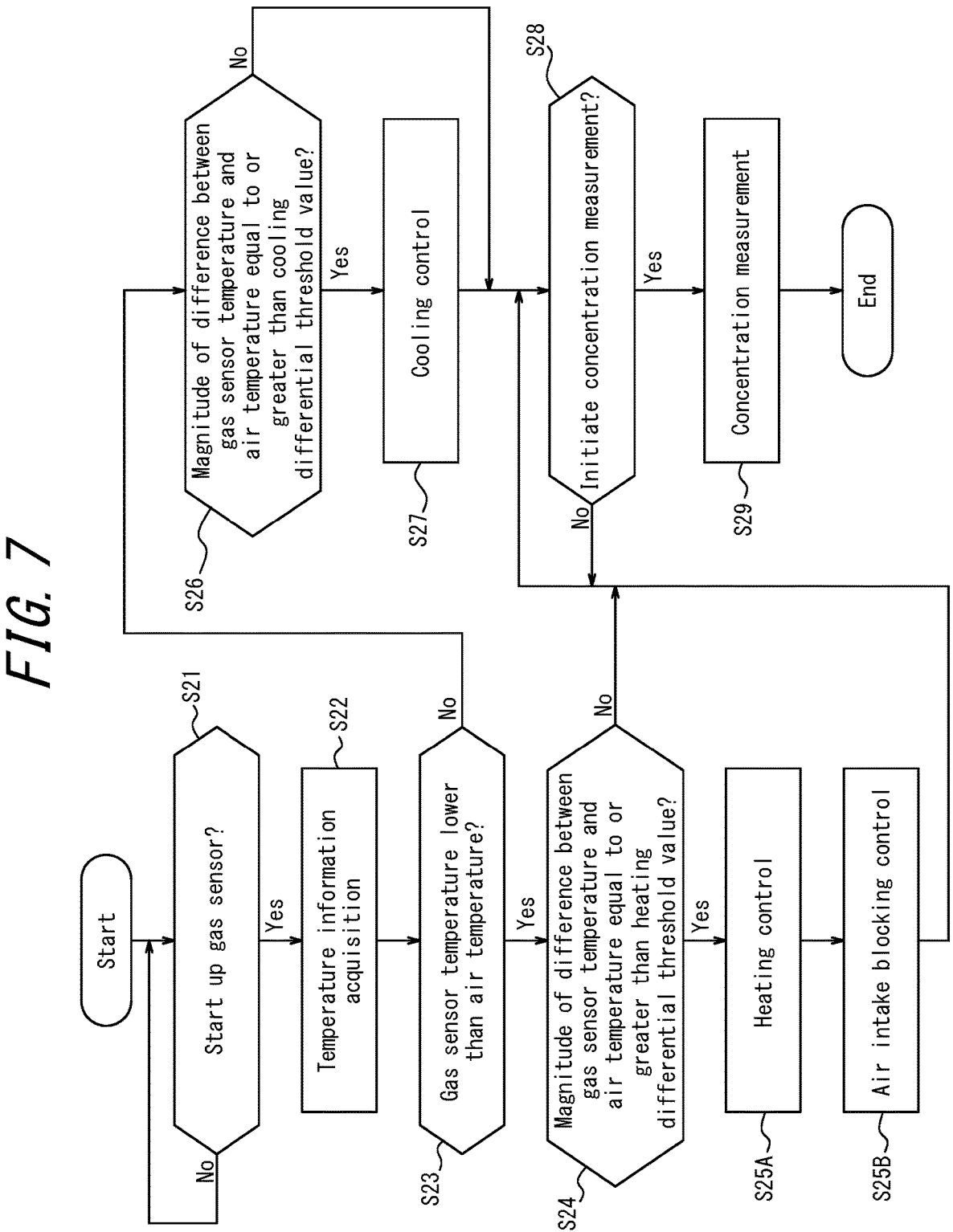
FIG. 7 is a flowchart illustrating an example of a control method according to a third embodiment of the present disclosure.

<Control Method>
FIG. 7 is a flowchart illustrating an example of an operation control method performed by the control device 20 of the gas sensor system 1 according to the present embodiment. The gas sensor system 1 waits (No in Step S21) until it acquires a startup signal. In the present embodiment, the startup signal to start up the gas sensor 10 is a signal from the control device of the vehicle that is transmitted by the control device of the vehicle with door unlocking as a start point.

The control device 20 starts up the gas sensor 10 in a situation in which it has acquired a door unlocking signal (Yes in Step S21) and acquires temperature information (Step S22). In the present embodiment, the temperature information includes temperature information for the gas sensor 10 and temperature information for a space from which the air intake port takes in air.

In a situation in which the temperature of the gas sensor 10 is lower than the temperature of the space from which the air intake port takes in air (Yes in Step S23), the control device 20 proceeds to processing in Step S24. In a situation in which the temperature of the gas sensor 10 is equal to or higher than the temperature of the space from which the air intake port takes in air (No in Step S23), the control device 20 proceeds to processing in Step S26.

In a situation in which the magnitude of difference between the temperature of the gas sensor 10 and the temperature of the space from which the air intake port takes in air (i.e., a value obtained by subtracting the temperature of the gas sensor 10 from the temperature of the space from which the air intake port takes in air) is equal to or greater than a heating differential threshold value (Yes in Step S24), the control device 20 performs heating control (Step S25A) and air intake blocking control (Step S25B). This heating control is control of operating the heater 17 so as to heat the gas sensor 10 and controlling the fan 13 so as to not take in air as previously described. The temperature of the gas sensor 10 rises through this heating control, and condensation is prevented through blocking of air intake.

In a situation in which the magnitude of difference between the temperature of the gas sensor 10 and the temperature of the space from which the air intake port takes in air (i.e., a value obtained by subtracting the temperature of the space from which the air intake port takes in air from the temperature of the gas sensor 10) is equal to or greater than a cooling differential threshold value (Yes in Step S26), the control device 20 performs cooling control (Step S27). This cooling control is control of operating the fan 13 so as to cool the gas sensor 10 as previously described. The temperature of the gas sensor decreases through this cooling control.

In a situation in which preparation is complete after the heating control or the cooling control and the magnitude of difference between the temperature of the gas sensor 10 and the temperature of the space from which the air intake port takes in air is less than the heating differential threshold value (No in Step S24), the control device 20 waits (No in Step S28) until it acquires a signal to initiate alcohol concentration measurement. Moreover, in a situation in which the magnitude of difference between the temperature of the gas sensor 10 and the temperature of the space from which the air intake port takes in air is less than the cooling differential threshold value (No in Step S26), the control device 20 waits (No in Step S28) until it acquires a signal to initiate alcohol concentration measurement. In the present embodiment, the signal to initiate alcohol concentration measurement is a signal from the control device of the vehicle that indicates that the engine of the vehicle has started. This signal to initiate alcohol concentration measurement may be generated with a signal to start the engine as a start point.

In a situation in which the control device 20 has acquired a signal to initiate alcohol concentration measurement (Yes in Step S28), the control device 20 causes the gas sensor 10 to perform concentration measurement of the measurement target gas (Step S29). In a situation in which the control device 20 has acquired a signal to initiate alcohol concentration measurement before preparation is complete after the heating control, the control device 20 may continue the heating control or the cooling control and cause the concentration measurement of the measurement target gas to be performed once preparation is complete. Note that concentration measurement of the measurement target gas may, in and of itself, be performed during the cooling control. A concentration measurement result value may be treated as invalid until preparation is complete.

Note that in a case in which the gas sensor system 1 does not include the second temperature measurement section 15, for example, judgment may be performed using a cooling threshold value and a heating threshold value as described in the first embodiment and the second embodiment. The control device 20 may perform control such that the operation time of the fan 13 is not more than a fixed time in the cooling control and the heating control and processing is performed in a loop. The concentration measurement of the measurement target gas may include provisional measurement as a test run, for example, and processing in the flowchart in FIG. 7 may be performed repeatedly until measurement for obtaining a final judgment result is performed.

Moreover, the heating control and the cooling control may be performed in combination depending on the situation. For example, the cooling control may be performed in a situation in which the heating control has been performed first, but in which the temperature of the space from which the air intake port takes in air has subsequently become lower than the temperature of the gas sensor 10. As a specific example, the cooling control may be performed in a situation in which the gas sensor 10 has been heated during the winter, but in which cold air has entered the vehicle from outside when a door of the vehicle is opened for a person to get out, for example, resulting in a temperature difference of 10° C. or more. Moreover, the heating control may be performed in a situation in which cold air has entered the vehicle from outside, the gas sensor has been cooled by taking in this cold air from the air intake port, and it is judged that the temperature of the gas sensor may cause the formation of condensation by exhaled air. The heating control and the cooling control are performed while making adjustments such that condensation does not occur and such that temperature of the gas sensor stabilizes.

In this manner, through the configuration and processing set forth above, the gas sensor system 1, the control device 20, and the control method according to the present embodiment perform cooling control or heating control in accordance with the temperature of the gas sensor 10, before initiation of measurement. Therefore, the gas sensor system 1, the control device 20, and the control method according to the present embodiment enable high-accuracy measurement without causing a user to wait.

Although embodiments of the present disclosure have been described based on the various drawings and examples, it should be noted that a person of ordinary skill in the art could easily make various modifications and revisions based on the present disclosure. Accordingly, such modifications and revisions should also be considered to be included within the scope of the present disclosure. For example, functions and the like included in various constituent parts, etc., can be rearranged so long as they are logically consistent. Moreover, a plurality of constituent parts, etc., can be combined as a single part or can be split up.

Although a gas sensor system 1 that is used in a vehicle is given as an example in the above-described embodiments, no limitations are placed on the subject of installation of the gas sensor system 1. For example, the gas sensor system 1 may be used indoors and may prevent reduction of measurement accuracy due to condensation. As a specific example, the gas sensor 10 may be provided in a kitchen that includes a ventilation fan, for example, and may prevent reduction of measurement accuracy through the configuration and processing set forth above in a situation in which condensation can arise due to hot and humid air being taken in due to boiling of water or the like.

The invention claimed is:

1. A gas sensor system comprising:
a gas sensor that performs concentration measurement of a measurement target gas in air;
a reception section that receives a startup signal from externally to the gas sensor system;
an air intake port and an air discharge port that are connected to the gas sensor;
at least one fan for performing air intake and air discharge from the air intake port and the air discharge port; and
a control device that starts up the gas sensor through reception of the startup signal, that acquires temperature information for the gas sensor, and that, based on the temperature information for the gas sensor, performs cooling control of operating the fan so as to cool the gas sensor from startup of the gas sensor, before initiation of the concentration measurement, wherein
the control device acquires temperature information for a space from which the air intake port takes in air and performs the cooling control based on the temperature information for the gas sensor and the temperature information for the space from which the air intake port takes in air.

2. The gas sensor system according to claim 1, wherein the control device performs the cooling control in a situation in which a temperature of the gas sensor is equal to or higher than a cooling threshold value.

3. The gas sensor system according to claim 1, wherein the control device performs the cooling control in a situation in which a magnitude of difference between a temperature of the gas sensor and a temperature of the space from which the air intake port takes in air is equal to or greater than a cooling differential threshold value.

4. The gas sensor system according to claim 3, wherein the cooling differential threshold value is 5° C. or higher.

5. The gas sensor system according to claim 1, wherein the control device sets operation time of the fan as not more than a fixed time in the cooling control.

6. The gas sensor system according to claim 1, wherein the control device stops the cooling control based on temperature information for the gas sensor in the cooling control.

7. The gas sensor system according to claim 1, wherein the control device stops operation of the fan based on a signal from externally to the gas sensor system in the cooling control.

8. The gas sensor system according to claim 1, wherein the gas sensor system is a system installed in a vehicle, and the reception section receives the startup signal from a control device of the vehicle in response to an operation of the vehicle and starts up the gas sensor.

9. The gas sensor system according to claim 8, wherein the operation of the vehicle includes door unlocking of the vehicle.

10. The gas sensor system according to claim 1, further comprising a transmission section that transmits a signal indicating that preparation for the concentration measurement is complete.

11. The gas sensor system according to claim 10, further comprising a notification section that notifies a user that preparation for the concentration measurement is complete based on the signal of the transmission section.

12. A gas sensor system comprising:

a gas sensor that performs concentration measurement of a measurement target gas in air;

a reception section that receives a startup signal from externally to the gas sensor system;

an air intake port and an air discharge port that are connected to the gas sensor;

at least one fan for performing air intake and air discharge from the air intake port and the air discharge port; and a control device that starts up the gas sensor through reception of the startup signal, that acquires temperature information for the gas sensor, and that, based on the temperature information for the gas sensor, performs cooling control of operating the fan so as to cool the gas sensor from startup of the gas sensor, before initiation of the concentration measurement, wherein the control device sets operation time of the fan as not more than a fixed time in the cooling control.

13. The gas sensor system according to claim 12, wherein the control device performs the cooling control in a situation in which a temperature of the gas sensor is equal to or higher than a cooling threshold value.

14. The gas sensor system according to claim 12, wherein the control device stops the cooling control based on temperature information for the gas sensor in the cooling control.

15. The gas sensor system according to claim 12, wherein the control device stops operation of the fan based on a signal from externally to the gas sensor system in the cooling control.

16. The gas sensor system according to claim 12, wherein the gas sensor system is a system installed in a vehicle, and the reception section receives the startup signal from a control device of the vehicle in response to an operation of the vehicle and starts up the gas sensor.

17. The gas sensor system according to claim 16, wherein the operation of the vehicle includes door unlocking of the vehicle.

18. The gas sensor system according to claim 12, further comprising a transmission section that transmits a signal indicating that preparation for the concentration measurement is complete.

19. The gas sensor system according to claim 18, further comprising a notification section that notifies a user that preparation for the concentration measurement is complete based on the signal of the transmission section.

* * * * *